United States Patent [19]
Lin et al.

[11] Patent Number: 5,792,105
[45] Date of Patent: Aug. 11, 1998

[54] MULTICHANNEL BALLOON CATHETER FOR DELIVERING FLUID

[75] Inventors: Donna Lin, Weston; Ernest J. St. Pierre, South Attleboro, both of Mass.

[73] Assignee: Boston Scientific Corporation, Natick, Mass.

[21] Appl. No.: 712,331

[22] Filed: Sep. 11, 1996

[51] Int. Cl.⁶ ............................................. A61M 25/00
[52] U.S. Cl. ........................... 604/96; 604/53; 604/283
[58] Field of Search ............................... 604/96, 101, 280, 604/283, 49, 52, 53; 606/192, 193, 194

[56] References Cited

U.S. PATENT DOCUMENTS

| | | | |
|---|---|---|---|
| 5,254,089 | 10/1993 | Wang . | |
| 5,569,184 | 10/1996 | Crocker et al. | 604/53 |
| 5,599,306 | 2/1997 | Klein | 604/96 |
| 5,609,574 | 3/1997 | Klaplan et al. | 604/53 |
| 5,611,775 | 3/1997 | Machold et al. | 604/53 |
| 5,611,812 | 3/1997 | Skornia | 604/96 X |
| 5,613,946 | 3/1997 | McKeever | 604/49 X |

Primary Examiner—John D. Yasko
Attorney, Agent, or Firm—Fish & Richardson P.C.

[57] ABSTRACT

An inflatable medical device for delivering fluid internally to a patient comprising a catheter having a fluid delivery lumen communicating between a fluid entry port at its proximal end and a fluid delivery port on an external wall of the catheter and a hollow, inflatable balloon having at least one fluid transmitting conduit disposed between inner and outer balloon walls. The fluid transmitting conduit receives fluid from the fluid delivery port of the catheter and is connected to at least one outlet on the outer balloon wall. The inner balloon wall extends axially beyond the proximal terminus of the outer balloon wall to form an inner sleeve for attaching the inner balloon wall to the catheter. An outer collar is attached at its distal end to the outer balloon wall and at its proximal end to the catheter at a point proximal to the fluid delivery port. The outer collar forms a conduit between the fluid delivery port and the proximal opening of the fluid transmitting conduit of the balloon. The diameter of the outer collar decreases gradually, or in at least one discrete step, from an enlarged area to a proximal catheter attachment area.

16 Claims, 6 Drawing Sheets

MULTICHANNEL BALLOON CATHETER FOR DELIVERING FLUID

BACKGROUND OF THE INVENTION

This invention is in the general field of inflatable medical devices for delivering fluid (e.g., medication) internally to a patient, and more particularly, to inflatable medical devices with a thin-walled outer collar connecting a balloon to a multilumen catheter.

Inflatable medical devices used, for example, to expand an artery that has been narrowed by atherosclerotic lesion or stenosis, can also deliver medication internally to a patient. In general, such medical devices include an inflatable balloon disposed at a distal end of a multilumen catheter shaft. An inflation fluid is forced into the balloon so that the expansion of the balloon engages the surface of the artery to enlarge its cross section.

U.S. Pat. No. 5,254,089 (the '089 patent) describes a medication dispensing balloon catheter device that can simultaneously provide forcible expansion to a cross section of an artery and dispense a medication to the site that has been forcibly expanded. The entire disclosure of the '089 patent is hereby incorporated herein by reference. The device disclosed in the '089 patent has a catheter containing multiple lumens. One of the lumens is a medication-delivery lumen communicating between a medication entry port at its proximal end and a medication delivery port on the external wall of the catheter shaft. The catheter also includes a hollow, inflatable balloon with medication transmitting channels or conduits disposed between inner and outer balloon walls. The medication transmitting channels of the balloon receive medication from an outlet of the medication delivery lumen of the catheter. An outer collar spans from its proximal end (attached to the catheter at a point proximal to the medication delivery port), to its distal end (attached to the outer balloon wall). In that way, the collar forms the outer wall of a conduit between the medication delivery port of the catheter and the proximal openings of the medication transmitting conduits of the balloon.

SUMMARY OF THE INVENTION

One aspect of the invention generally features an inflatable medical device generally as described above, having a hollow, inflatable balloon with at least one fluid (medication) transmitting conduit, having an inner wall configured as follows. The fluid transmitting conduit of the balloon extends from a proximal opening for receiving fluid to at least one external outlet on balloon. The inner wall of the fluid transmitting conduit extends axially beyond the proximal terminus of the conduit outer wall, so that the inner wall forms an inner extension for attaching the inner wall to the external wall of the catheter at a position distal to the fluid delivery port of the catheter. An outer collar is attached at its distal end to the outer wall of the balloon's fluid transmitting conduit and the collar is attached at its proximal end to the external wall of the catheter at a point proximal to the fluid delivery port. Thus, fluid or medication is conveyed from the catheter delivery port of the catheter to the fluid transmitting conduit of the balloon through a closed path that is formed between the outer collar and the outer wall of the catheter.

Typically, the balloon has an inner balloon wall which serves as the inner wall of the fluid transmitting conduit, and an outer balloon wall which serves as the outer wall of the fluid transmitting conduit. The balloon includes at least two dividers which are spaced apart from each other and extend between the inner balloon wall and the other balloon wall. In that case, the fluid transmitting conduit is bounded by the inner balloon wall, the dividers, and the outer balloon wall.

Another aspect of the invention can be of benefit by itself or in combination with the first aspect. This second aspect of the invention generally features a device in which the outer collar has a distal balloon attachment area sized to surround and attach to the outer balloon wall and a radially enlarged area, immediately proximal to the balloon attachment area, having a diameter larger than the diameter of the balloon attachment area.

Both aspects of the invention are designed to reduce the opportunity for adhesive to clog the openings to the intrawall channels. The second embodiment in particular provides a space that can receive excess adhesive so that the adhesive is less likely to clog the fluid conduit(s) of the balloon.

In preferred embodiments of both aspects of the invention, the balloon includes multiple fluid transmitting channels or conduits spaced circumferentially around the balloon, each of which communicates with at least one outlet on the outer balloon wall. The balloon also includes dividers positioned between the inner and outer balloon walls to divide the conduits; the dividers may extend axially beyond the proximal terminus of the outer balloon wall, to further separate the conduit openings from the site of adhesive application.

The outer balloon wall may terminate in an outer sleeve of reduced diameter, to which the outer collar is attached, so the dividers extend axially at least as far as the outer sleeve of the balloon, forming multiple inlets for the fluid transmitting conduits at the terminus of the outer sleeve.

The outer collar may include a proximal catheter attachment area sized to surround and attach to the external wall of the catheter, and the diameter of the outer collar decreases gradually, or in at least one discrete step, from the enlarged area to the proximal catheter attachment area.

The device includes at least three adhesive layers: one attaching the inner balloon wall to the catheter, a second attaching the distal end of the outer collar to the outer balloon wall, and a third attaching the proximal end of the outer collar to the catheter at the point proximal to the fluid delivery port.

In another aspect, the invention generally features a method for making the above-described device by: attaching the inner sleeve of the balloon to the catheter; attaching the distal end of the outer collar to the outer balloon wall; and attaching the proximal end of the outer collar to the catheter at a point proximal to the fluid delivery port.

In yet another aspect, the invention features delivering medication or fluid internally to a patient with one of the devices described above by inflating the balloon and injecting fluid into the catheter at a fluid entry port so that the fluid flows through the fluid delivery lumen to the fluid delivery port, through the conduit formed by the outer collar and through the fluid transmitting conduit in the balloon to at least one outlet on the outer balloon wall.

The above features (particularly the balloon'inner sleeve and the shape of the outer collar, with its enlarged area and decreasing diameter) improve the manufacturability of the device. Adhesives are much less likely to seep into and clog the proximal opening of the balloon channel, because the opening is physically separated from the site of adhesion. In addition, the invention is easy to manufacture because the inner sleeve of the balloon and the outer collar can be joined to the catheter and the balloon using straightforward adhesive techniques.

Other aspects of the invention separately feature the balloon and the collar described above.

Other features and advantages will be apparent from the following drawings, description of the preferred embodiments and claims.

DETAILED DESCRIPTION

Figure 1:
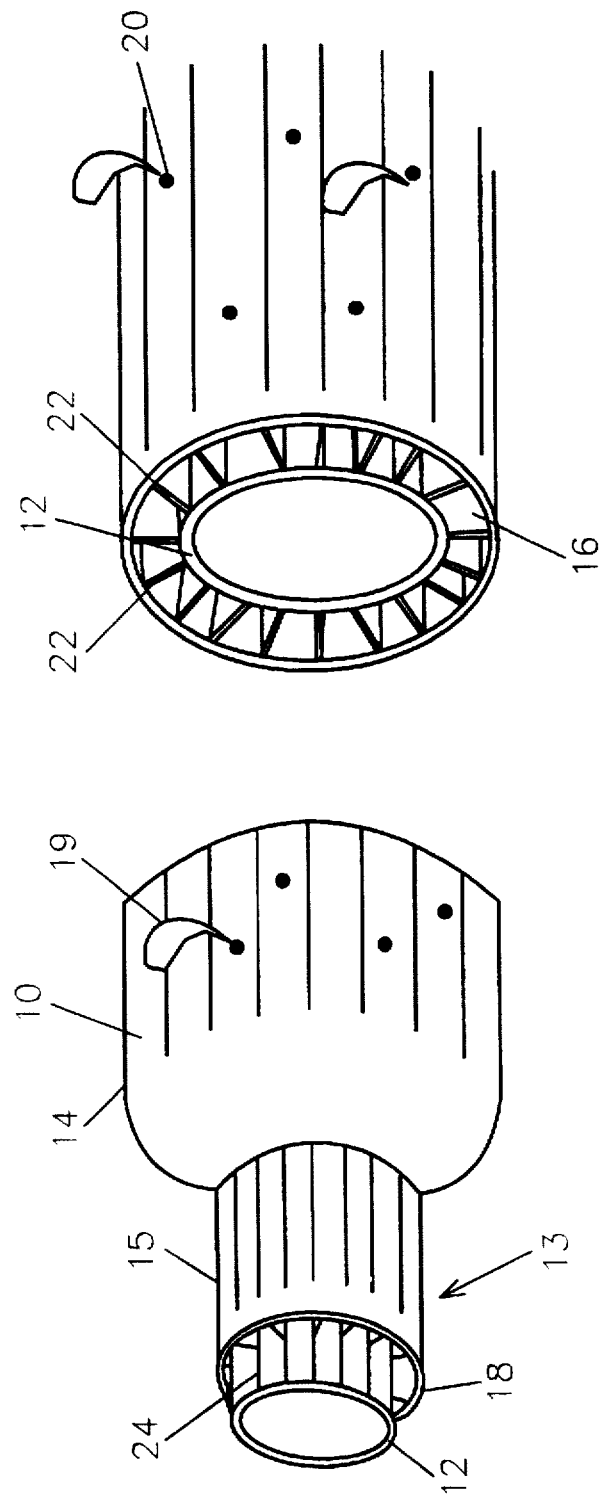
FIG. 1 is a perspective view of a portion of a multichannel balloon, shown broken away and partially in section.

Referring to FIG. 1, a balloon 10 has an inner balloon wall 12, an outer balloon wall 14, and dividers 17 which define channels or conduits 16 therebetween. Channels 16 are spaced circumferentially around balloon 10. Each of channels 16 has a proximal opening 18 into which medication enters, and each channel terminates in an outlet 20 on outer balloon wall 14, through which medication 19 is delivered. Dividers 22 maintain clearance between the inner and outer balloon walls. Balloon 10 may be a medication dispensing balloon generally as described in the '089 patent.

The proximal end of balloon terminates in a region 13 of reduced diameter. Inner balloon wall 12 extends axially beyond the proximal terminus of outer balloon wall 14 to form an inner sleeve 24 for attaching inner balloon wall 12 to a catheter. In addition, the proximal end of outer balloon wall 14 forms an outer sleeve 15. Dividers 22 extend axially at least as far as outer sleeve 15 of balloon 10 and may extend axially beyond outer sleeve 15.

Figure 2:
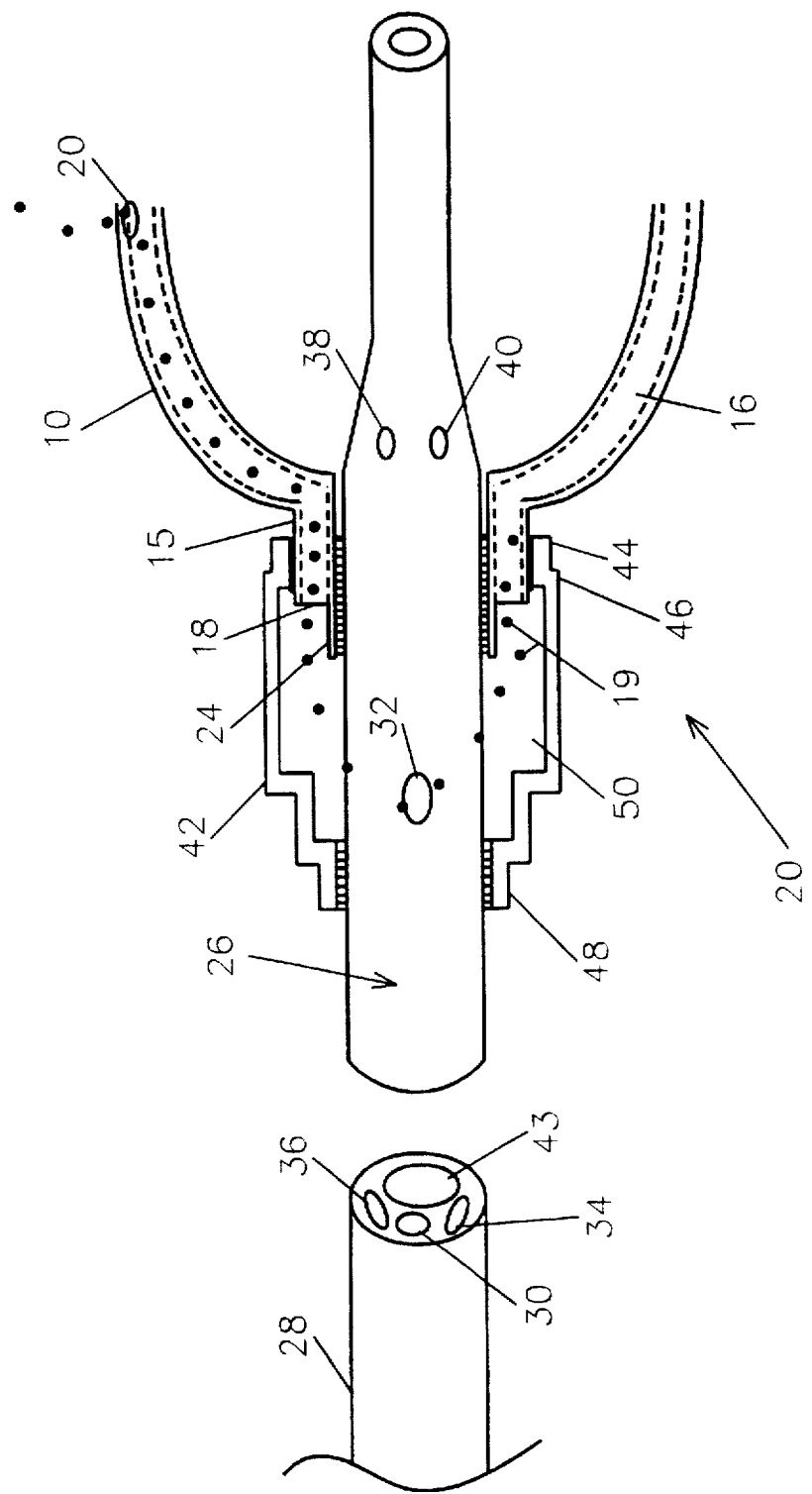
FIG. 2 is a sectional view of a multichannel balloon catheter with the multichannel balloon of FIG. 1.

In FIG. 2, balloon 10 of FIG. 1 is shown as part of a multichannel balloon catheter device 27. Device 27 has a tapered catheter 26 with an external wall 28 having multiple lumens disposed therein. Lumen 30 is used to deliver medication to balloon 10, and it is connected to a medication delivery port 32 on external wall 28 of catheter 26. Medication 19 flows out of port 32 to openings 18 in the balloon channel. Lumens 34 and 36 deliver inflation fluids to balloon 10, and they are connected to inflation-fluid delivery ports 38, 40 on external wall 28 of catheter 26. Lumen 43 carries a guide wire (not shown) extending through catheter 26.

A thin-walled outer collar 42 has a distal balloon attachment area 44 sized to surround and attach to outer sleeve 15 and an enlarged area 46 immediately proximal to balloon attachment area 44. Enlarged area 46 has a diameter larger than the diameter of the balloon attachment area 44. Outer collar 42 also has a proximal catheter attachment area 48 sized to surround and attach to external wall 28 of catheter 26. The diameter of outer collar 42 decreases in discrete steps from enlarged area 46 to catheter attachment area 48. Enlarged area 48 defines space 50.

Figure 3:
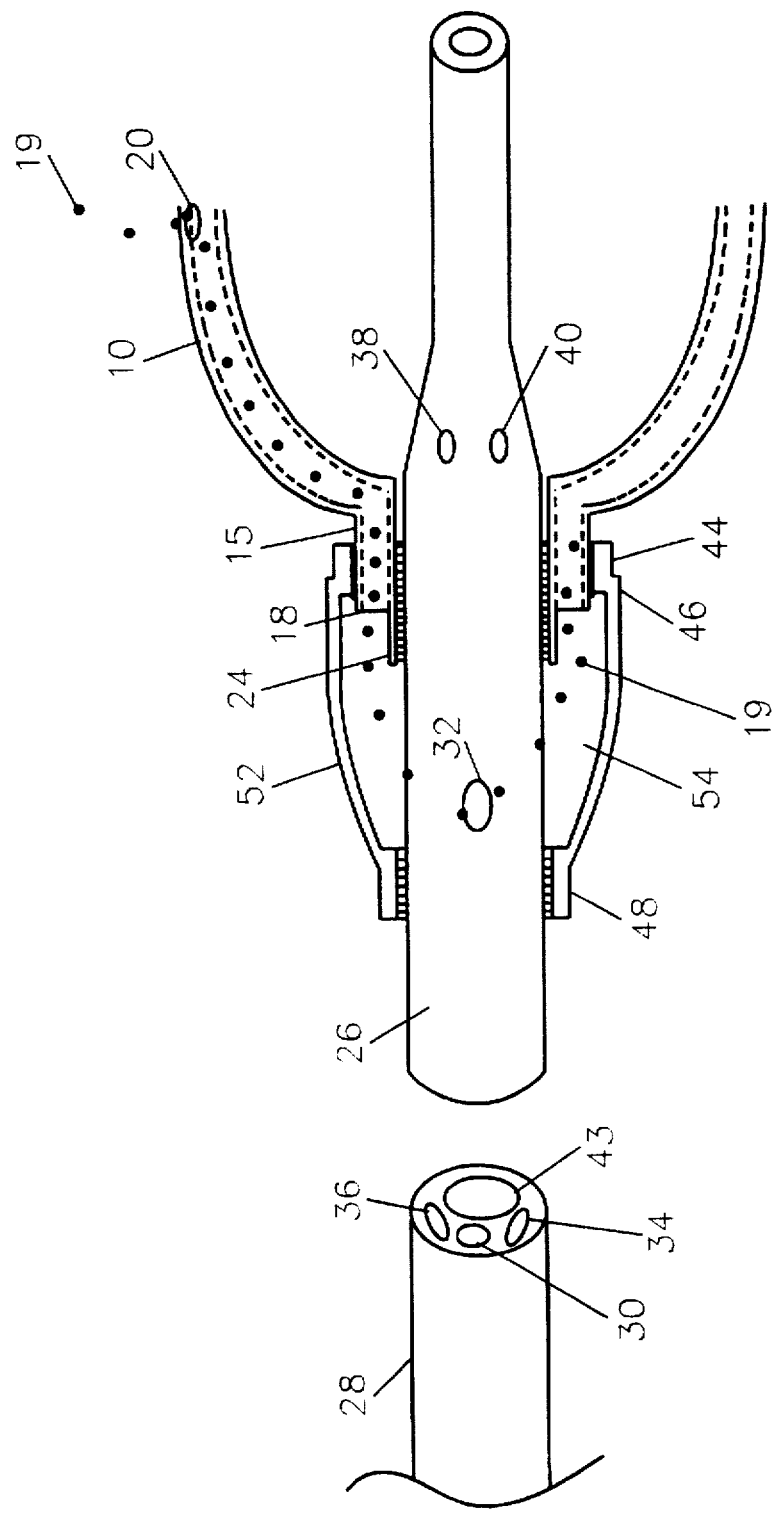
FIG. 3 is a perspective view of another embodiment of a multichannel balloon catheter with the multichannel balloon of FIG. 1.

While it is somewhat easier to manufacture the collar with a discrete step, other collar configurations are possible. As shown in the alternative embodiment of FIG. 3, the diameter of outer collar 52 can decrease gradually from enlarged area 46 to catheter attachment area 48, so as to create a space 54.

Figure 4A:
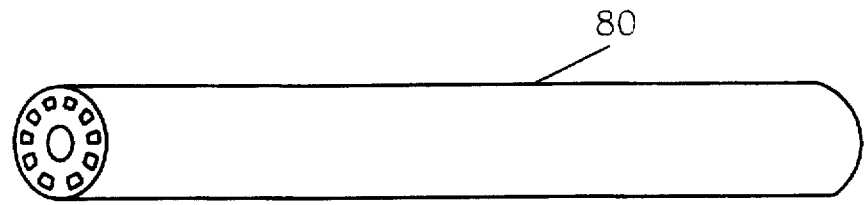
FIGS. 4(a)–4(f) show the steps of manufacturing a multichannel balloon.
Figure 4B:
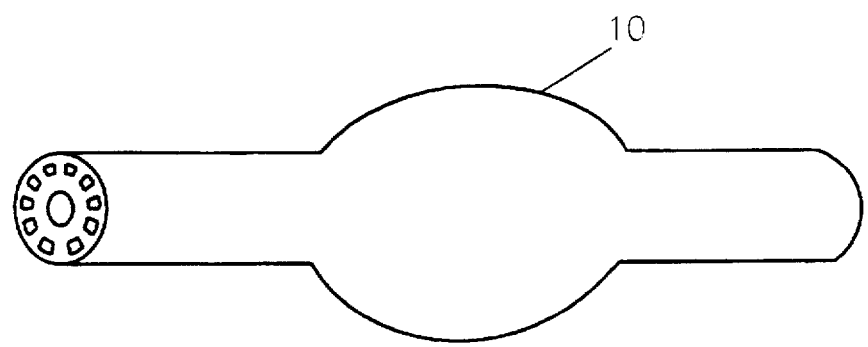
Figure 4C:
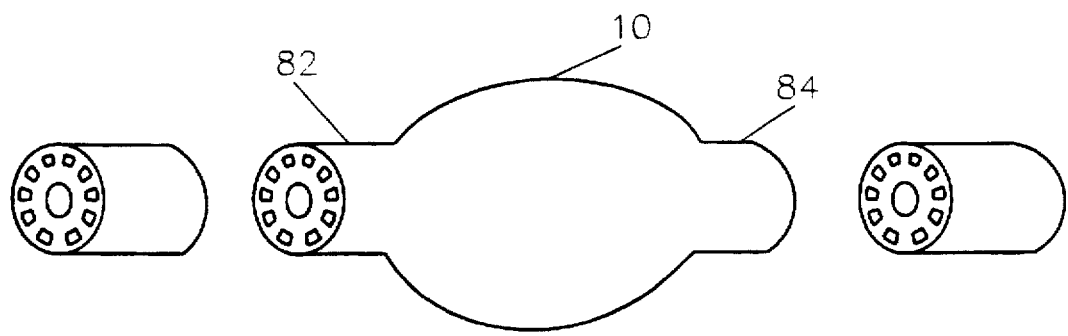

FIGS. 4(a)–4(f) show the steps of manufacturing a multichannel balloon. Typically, a balloon may be formed by applying heat and pressure to, for example, a 12 inch extruded plastic tube having one or more lumens. In addition, the balloon may be made by single or coextruding two or more layers. In one embodiment, balloon 10 is formed by applying heat and pressure to a plastic tube 80 having eighteen channels disposed around a central lumen, as shown in FIGS. 4(a) and 4(b). After balloon 10 is formed, the ends of plastic tube 80 on either side of balloon 10 are cut to form a proximal sleeve 82 and a distal sleeve 84 of balloon 10, as shown in FIG. 4(c).

Figure 4D:
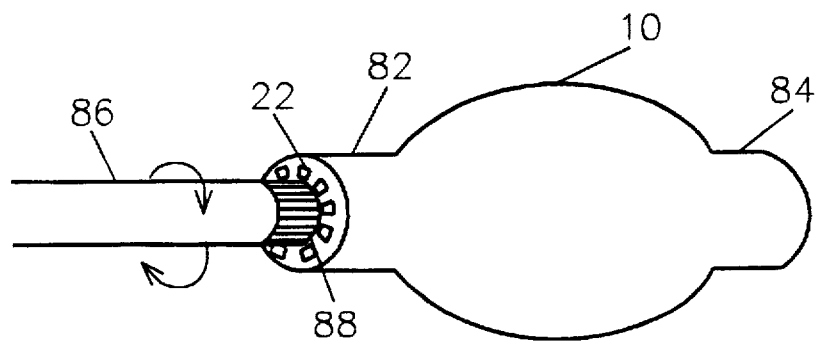
Figure 4E:
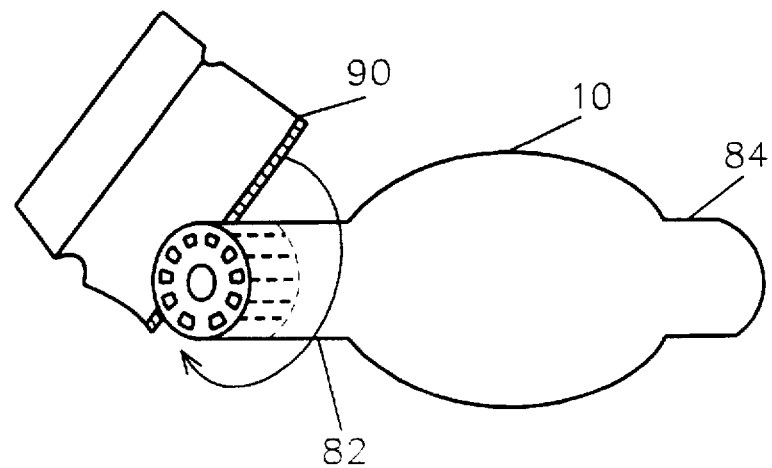
Figure 4F:
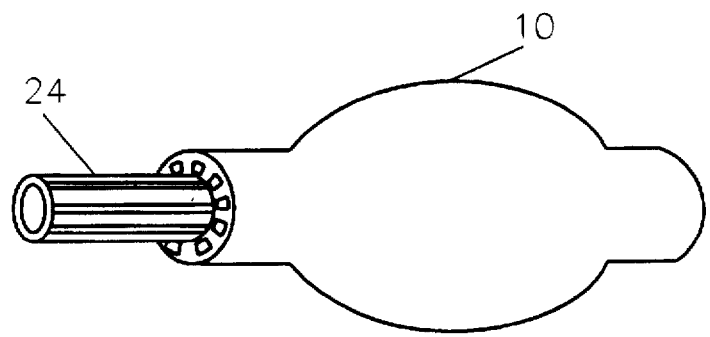

Referring to FIG. 4(d), a stainless steel tube 86 with a circular cutting edge 88 is advanced approximately 1 mm into proximal sleeve 82 of balloon 10 between its inner and outer balloon walls and rotated, thereby cutting dividers 22. Referring to FIG. 4(e), a straight cutting edge 90, perpendicular to the balloon axis, is used to cut the outer balloon wall in order to separate the outer balloon wall from the inner balloon wall, thereby forming inner sleeve 24, as shown in FIG. 4(f).

Figure 5A:
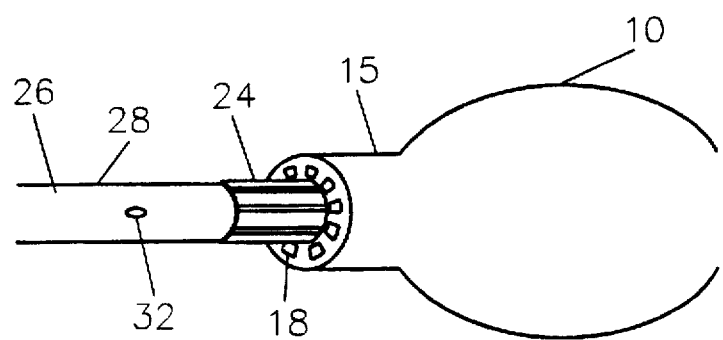
FIGS. 5(a) and 5(b) show the steps of manufacturing a multichannel balloon catheter.
Figure 5B:
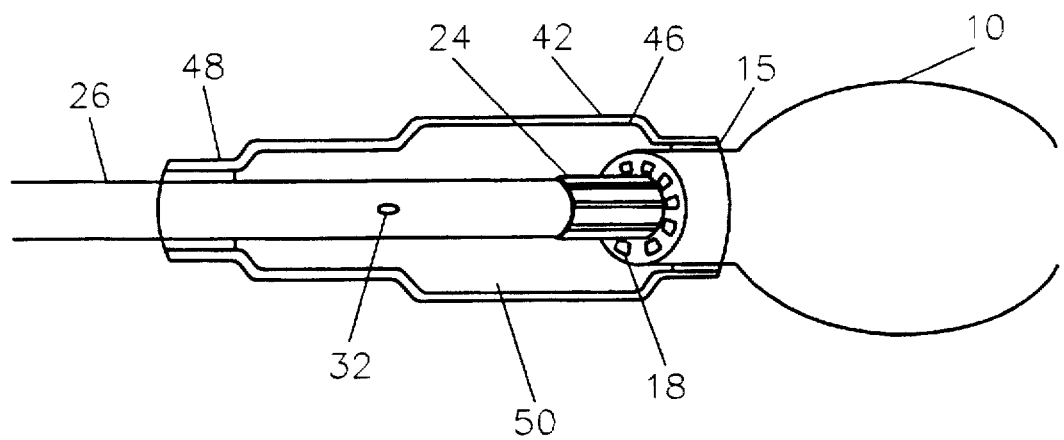

FIGS. 5(a) and 5(b) show the steps of manufacturing a multichannel balloon catheter. Balloon 10 is disposed at the distal end of catheter 26, and inner sleeve 24 of balloon 10 is glued to external wall 28 of catheter 26, as shown in FIG. 5(a). Referring to FIG. 5(b), outer collar 42 is glued at its distal end to outer sleeve 15 of balloon 10 and at its proximal end to external wall 28 of catheter 26 at a point proximal to medication delivery port 32, thereby forming a conduit between medication delivery port 32 and proximal opening 18 of each channel 16.

Outer collar 42 is made of a material capable of being bonded to the balloon and the outer catheter wall, such as polyethylene terapthalate, polyethylene, nylon, polyethylene napthalate, TPE (engineering thermoplastic elastomers) and coextruded polymers (two or more layers). The glue is a low viscosity adhesive capable of curing rapidly to form flexible, transparent bonds when exposed to ultraviolet radiation or visible light of sufficient intensity, such as acrylated urethane.

The diameter of outer collar 42 decreases from enlarged region 46 to catheter attachment region 48. The space 50 receives excess adhesive. Inner sleeve 24 of balloon 10 and the shape of outer collar 42, with its enlarged area 46 and decreasing diameter, glue is less likely to seep into proximal opening 18 of channel 16 and thus clogging channel 16.

Catheter 26 is inserted through a lumen of a patient's body to deliver medication internally to the patient, such as to the patient's vascular system, neurovascular system, auditory system, urinary tract and prostate, as well as the biliary, alimentary, endovascular and obstetrical/gynecological systems. Such medication includes drugs, contrast agents, drying agents, radioactive agents, chemotherapeutic agents, photodynamic therapy (PDT) agents and other substances.

Those skilled in the art will recognize that other embodiments are within the following claims. For example, the catheter shaft may be straight instead of tapered.

What is claimed is:

1. An inflatable medical device for delivering fluid internally to a patient comprising:
    a) a catheter comprising an external wall and multiple lumens disposed therein, at least one of the lumens being a fluid delivery lumen communicating with a fluid delivery port on the external wall of the catheter;
    b) a hollow, inflatable balloon having at least one fluid transmitting conduit,
        1) the fluid transmitting conduit extending from a proximal opening for receiving fluid to at least one external outlet on balloon, 2) the fluid transmitting conduit having an inner wall and an outer wall, the inner wall extending axially beyond the proximal terminus of the outer wall to form an inner extension for attaching the inner fluid transmitting conduit wall to the external wall of the catheter; and c) an outer collar attached at its distal end to the outer wall of the balloon's fluid transmitting and at its proximal end to the external wall of the catheter at a point proximal to the fluid delivery port, whereby fluid is conveyed from the catheter's fluid delivery port to the fluid transmitting conduit of the balloon through a closed path that is formed between the outer collar and the outer wall of the catheter.

2. The device of claim 1 in which the balloon has an inner balloon wall and an outer balloon wall, the fluid transmitting conduit being positioned between the inner balloon wall and the outer balloon wall.

3. The device of claim 1 in which the balloon has
a) an inner balloon wall which serves as the inner wall of the fluid transmitting conduit, and an outer balloon wall which serves as the outer wall of the fluid transmitting conduit, and
b) at least two dividers which are spaced apart from each other and which extend between the inner balloon wall and the other balloon wall,
whereby the fluid transmitting conduit is bounded by the inner balloon wall, the dividers, and the outer balloon wall.

4. The device of claim 3 wherein the outer collar has a distal balloon attachment area sized to surround and attach to the outer balloon wall and a radially enlarged area immediately proximal to the balloon attachment area, the enlarged area having a diameter larger than the diameter of the distal balloon attachment area of the collar.

5. An inflatable medical device for delivering fluid internally to a patient comprising:
(a) a catheter comprising an external wall and multiple lumens disposed therein, at least one of the lumens being a fluid delivery lumen communicating with a fluid delivery port on the external catheter wall;
(b) a hollow, inflatable balloon comprising inner and outer balloon walls and having at least one fluid transmitting conduit disposed between the inner and outer balloon walls, the fluid transmitting conduit comprising a proximal opening for receiving fluid from the fluid delivery port of the catheter and the fluid transmitting conduit being connected to at least one outlet on the outer balloon wall, the balloon comprising an inner sleeve for attaching the inner balloon wall to the catheter; and
(c) an outer collar attached at its distal end to the outer balloon wall and at its proximal end to the catheter at a point proximal to the fluid delivery port, the outer collar thereby forming a conduit between the fluid delivery port and the proximal opening of the fluid transmitting conduit of the balloon, the outer collar having a distal balloon attachment area sized to surround and attach to the outer balloon wall and a radially enlarged area immediately proximal to the balloon attachment area, the enlarged area having a diameter larger than the diameter of the balloon attachment area.

6. The device of claim 1 or claim 5 wherein the balloon comprises multiple fluid transmitting conduits spaced circumferentially around the balloon, each of the fluid transmitting conduits communicating with at least one outlet on the outer balloon wall, the balloon comprising dividers positioned between the inner and outer balloon walls to divide the fluid transmitting conduits.

7. The device of claim 6 wherein the outer balloon wall terminates in an outer sleeve to which the outer collar is attached, and the dividers extend axially at least as far as the outer sleeve of the balloon, forming multiple inlets for the fluid transmitting conduits at the terminus of the outer sleeve.

8. The device of claim 7 in which the dividers extend axially beyond the outer sleeve of the balloon.

9. The device of claim 4 or claim 5, wherein the outer collar includes a proximal catheter attachment area sized to surround and attach to the external wall of the catheter.

10. The device of claim 9 in which the diameter of the outer collar decreases gradually from the enlarged area to the proximal catheter attachment area.

11. The device of claim 9 in which the diameter of the outer collar decreases in at least one discrete step from the enlarged area to the proximal catheter attachment area.

12. The device of claim 1 or claim 5 in which the device comprises a first adhesive layer attaching the inner balloon wall to the catheter, a second adhesive layer attaching the distal end of the outer collar to the outer balloon wall, and a third adhesive layer attaching the proximal end of the outer collar to the catheter at the point proximal to the fluid delivery port.

13. A method for making the device of claim 1 or claim 5 comprising:
attaching the inner sleeve of the balloon to the catheter;
attaching the distal end of the outer collar to the outer balloon wall and attaching the proximal end of the outer collar to the catheter at a point proximal to the fluid delivery port, the outer collar thereby forming a conduit between the fluid delivery port and the proximal opening of the fluid transmitting conduit of the balloon.

14. A method for delivering fluid internally to a patient with the device of claim 1 or claim 5 comprising:
providing the device of claim 1 or claim 5,
inflating the balloon; and
injecting fluid into the catheter at the fluid entry port so that the fluid flows through the fluid delivery lumen to the fluid delivery port, through the conduit formed by the outer collar and through the fluid transmitting conduit to at least one outlet on the outer balloon wall.

15. A collar for connecting a catheter comprising a fluid delivery lumen to a balloon that comprises fluid transmitting channels, the collar comprising:
(a) a distal balloon attachment area sized to surround and attach to the outer balloon wall; and
(b) a radially enlarged area immediately proximal to the balloon attachment area, the enlarged area having a diameter larger than the diameter of the balloon attachment area.

16. A balloon for connection to a catheter to form an inflatable medical device for delivering fluid internally to a patient, the balloon comprising at least one fluid transmitting conduit,
1) the fluid transmitting conduit extending from a proximal opening for receiving fluid to at least one external outlet on balloon,
2) the fluid transmitting conduit having an inner wall and an outer wall, the inner wall extending axially beyond the proximal terminus of the outer wall to form an inner extension for attaching the inner wall to the external wall of the catheter.

* * * * *